United States Patent
Tian (10) Patent No.: US 11,730,594 B2
(45) Date of Patent: Aug. 22, 2023

(54) BALLOON-EXPANDABLE HEART VALVE SYSTEM AND METHOD OF IMPLANTATION

(71) Applicant: Vitae LLC, Irvine, CA (US)

(72) Inventor: Bin Tian, Irvine, CA (US)

(73) Assignee: Vitae LLC, Irvine, CA (US)

( * ) Notice: Subject to any disclaimer, the term of this patent is extended or adjusted under 35 U.S.C. 154(b) by 0 days.

(21) Appl. No.: 17/693,379

(22) Filed: Mar. 13, 2022

(65) Prior Publication Data
US 2022/0192825 A1  Jun. 23, 2022

Related U.S. Application Data

(63) Continuation of application No. 16/871,005, filed on May 10, 2020, now Pat. No. 11,278,403.

(51) Int. Cl.
*A61F 2/24* (2006.01)
*A61F 2/958* (2013.01)

(52) U.S. Cl.
CPC .......... *A61F 2/2433* (2013.01); *A61F 2/2418* (2013.01); *A61F 2/958* (2013.01); *A61F 2/2409* (2013.01); *A61F 2/2436* (2013.01); *A61F 2250/0029* (2013.01); *A61F 2250/0039* (2013.01)

(58) Field of Classification Search
CPC .... A61F 2/2409; A61F 2/2418; A61F 2/2433; A61F 2/958
See application file for complete search history.

(56) References Cited

U.S. PATENT DOCUMENTS

2017/0079793 A1* 3/2017 Maimon ............... A61F 2/2418

OTHER PUBLICATIONS

International Preliminary Report dated Nov. 15, 2022 for corresponding PCT Application No. PCT/US2021/031153.

\* cited by examiner

*Primary Examiner* — Suba Ganesan
(74) *Attorney, Agent, or Firm* — Raymond Sun (57) ABSTRACT

A system has a heart valve assembly that includes a stent-frame having an anchoring section and an outflow section, with the anchoring section having a distal annulus section and a support section that is positioned between the distal annulus section and the outflow section. The distal annulus section has a concave inflection. A leaflet assembly is stitched to the anchoring section. The system also includes a balloon on which the heart valve assembly is crimped, the balloon having a central valve contact portion that has an outflow portion, a neck portion, and a central portion between the outflow portion, and the neck portion. The outflow portion of the balloon receives the outflow section of the stent-frame, the central portion of the contact portion of the balloon receives the support section of the stent-frame, and the neck portion receives the annulus section of the stent-frame.

1 Claim, 11 Drawing Sheets

BALLOON-EXPANDABLE HEART VALVE SYSTEM AND METHOD OF IMPLANTATION

BACKGROUND OF THE INVENTION

1. Field of the Invention

The present invention is directed to systems for implanting expandable prosthetic heart valves and, in particular, a prosthetic heart valve and a shaped expansion member for deploying the heart valve.

2. Description of the Prior Art

Minimally-invasive heart valve replacement has become very common in recent times. Such minimally-invasive heart valve replacement typically involve a self-expandable or a balloon-expandable stent integrated with a bioprosthetic valve having flexible leaflets, with the stent-valve device deployed across the native diseased valve to permanently hold the valve open, thereby alleviating a need to excise the native valve. These devices are designed for percutaneous delivery in a cardiac catheterization laboratory under local anesthesia using fluoroscopic guidance, thereby avoiding general anesthesia and open-heart surgery.

These expandable heart valves use either balloon- or self-expanding stents as anchors. The uniformity of contact between the expandable valve and surrounding annulus, with or without leaflets, should be such that no paravalvular leakage (PVL) occurs, and therefore proper expansion is very important. Perhaps more problematic is the quality of coaptation of the leaflets once the valve is expanded into place. Coaptation refers to the degree that the individual flexible leaflets come together in the valve orifice to occlude the back flow. If the leaflets do not quite meet, which could happen if the flexible valve is not expanded properly, regurgitation may occur. These and other issues make proper implant of the valve extremely critical. However, unlike open-heart surgery, the implant site is not directly accessible or visible and the valve must be implanted remotely at the end of a catheter or cannula under indirect visualization (e.g., fluoroscopic imaging).

Balloon-expandable heart valves typically require expansion with a cylindrical balloon of clear nylon. The inflation fluid consists of saline mixed with a more viscous contrast media. The inherent viscosity of the mixture increases the inflation/deflation time, which is undesirable because the balloon occludes the target annulus when in use, and more and more procedures are being done off-pump, or on a beating heart.

In addition, PVL remains as one of the major issues post transcatheter valve implant. Various designs have been developed but have proven to be unable to eliminate PVL.

Thus, there is a need for implantation systems and techniques that reduce the time for and increase the chances of a successful implant, while minimizing or eliminating PVL.

SUMMARY OF THE DISCLOSURE

The present invention provides a system and method for deploying balloon-expandable prosthetic heart valves so that they assume their desired operational shape. The system includes a prosthetic heart valve and an expansion member that accommodates non-uniform expansion resistance in the heart valve to expand to its desired tubular or other shape.

The prosthetic heart valve assembly according to the present invention provides an outflow (aortic) end of the stent-frame that is slightly larger than that of the inflow (ventricular) end. This design can maximize the valve geographic effective orifice area (EOA) and reduce the stagnant blood near the cupid area during the diastolic cardiac phase when the valve is closed. This design can also reduce the risk of patient prosthetic mismatch due to the increase in EOA and can also reduce the valve related thrombosis.

To accomplish the objectives of the present invention, there is provided a system that has a heart valve assembly that includes a stent-frame having an anchoring section and an outflow section, with the anchoring section having a distal annulus section and a support section that is positioned between the distal annulus section and the outflow section. The distal annulus section is defined by a single distal row of cells that has a distal-most annular ring of alternating peaks and valleys, with the distal row of cells having a concave inflection. A leaflet assembly is stitched to the anchoring section. The system also includes a balloon on which the heart valve assembly is crimped, the balloon having a proximal section and a distal section, and a central valve contact portion positioned between the proximal and distal sections. The contact portion has an outflow portion, a neck portion, and a central portion between the outflow portion and the neck portion, and the neck portion has an inflection zone that corresponds in size and shape with the concave inflection of the distal annulus section. The outflow portion of the balloon receives the outflow section of the stent-frame, the central portion of the contact portion of the balloon receives the support section of the stent-frame, and the neck portion receives the annulus section of the stent-frame.

The expansion member according to the present invention provides a mechanism to restore the stent-frame into its initial-designed operating shape by a unique balloon design. Specifically, the stent-frame is pre-set in a desirable geometry as mentioned above while the balloon is also pre-set in a shape that is matched with the stent-frame. Therefore, during the deployment of the heart valve assembly, the stent-frame can be restored in its preset shape when fully expanded.

The present invention provides a method for deploying the heart valve assembly using the expansion member or balloon of the present invention. The heart valve assembly is mounted on to the balloon in a manner where the outflow portion of the balloon receives the outflow section of the stent-frame, the central portion of the contact portion of the balloon receives the support section of the stent-frame, and the neck portion receives the annulus section of the stent-frame. The combined balloon and the mounted heart valve assembly are then delivered to the aortic annulus, and the balloon is expanded to cause the aortic annulus to be received inside the concave inflection.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides an improved system and method for deploying a balloon-expandable heart valve so that it can assume its intended operating shape and better fits into a patient's aortic annulus and local anatomy. The designs in the present invention have two advantages in comparison to current balloon expandable transcather heart valves (THVs). First, the super-annulus valve design increases the geographic EOA of the valve and increases the space between the bioprosthetic leaflets and the stent-frame to reduce the stagnant blood flow. Second, the unique stent-frame design at the inflow end provides a better fit to the native aortic annulus, thereby reducing the risk of PVL. The expandable heart valve assembly according to the present invention has a stent-frame that supports inner flexible leaflets that provide fluid occluding surfaces. The heart valve assembly is designed to expand from a compressed state for delivery into an operating shape that ensures good coaptation of the leaflets.

The present invention described herein provides a solution that ensures proper deployment of a balloon-expandable prosthetic heart valve assembly having a stent-frame that undergoes plastic deformation from one size to a larger size. Examples of stent-frame materials include, but are not limited to, stainless steel, Elgiloy (an alloy primarily composed of cobalt, chromium and nickel), titanium alloys, and other specialty metals.

The present invention accommodates heart valves of non-constant expansion resistance. That is, the balloon-expandable prosthetic heart valve assembly has one end, typically the inflow end, that possesses a greater number of structural components, including stitching. The heart valve assembly is mounted over an expansion balloon, delivered to the implant site, and the balloon is inflated. Because of the axial constructional non-uniformity of the heart valve assembly, expansion of the balloon will cause greater or earlier radial expansion at whichever part of the heart valve assembly presents the least expansion resistance. Typically, the inflow end presents greater resistance to expansion, resulting in the outflow end experiencing greater and faster expansion. The present invention provides a unique balloon shape to accommodate this constructional non-uniformity, so that the heart valve assembly expands to its designed operational shape. The final shape of the stent-frame can have a non-linear profile to adapt to the anatomy of the valve annulus.

Figure 1:
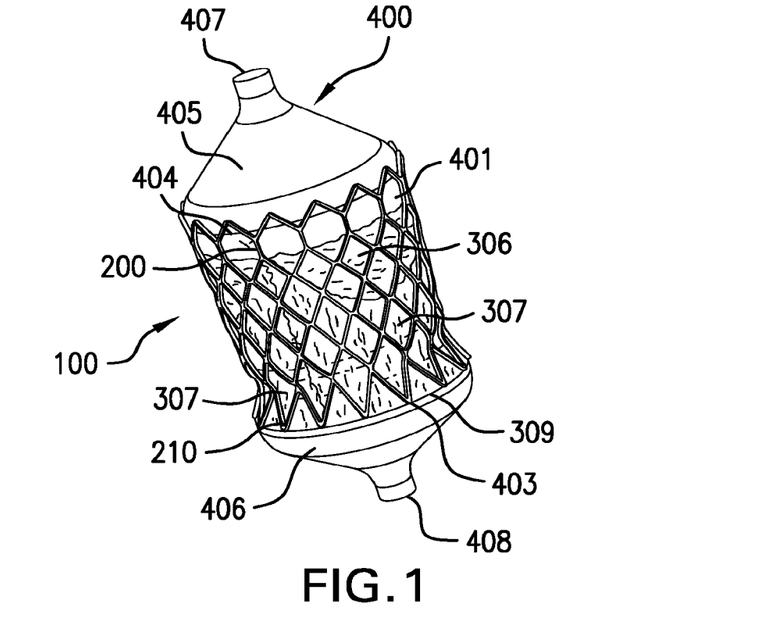
FIG. 1 is a perspective view of a heart valve assembly carried on an expansion member according to one embodiment of the present invention shown in an expanded configuration.
Figure 2:
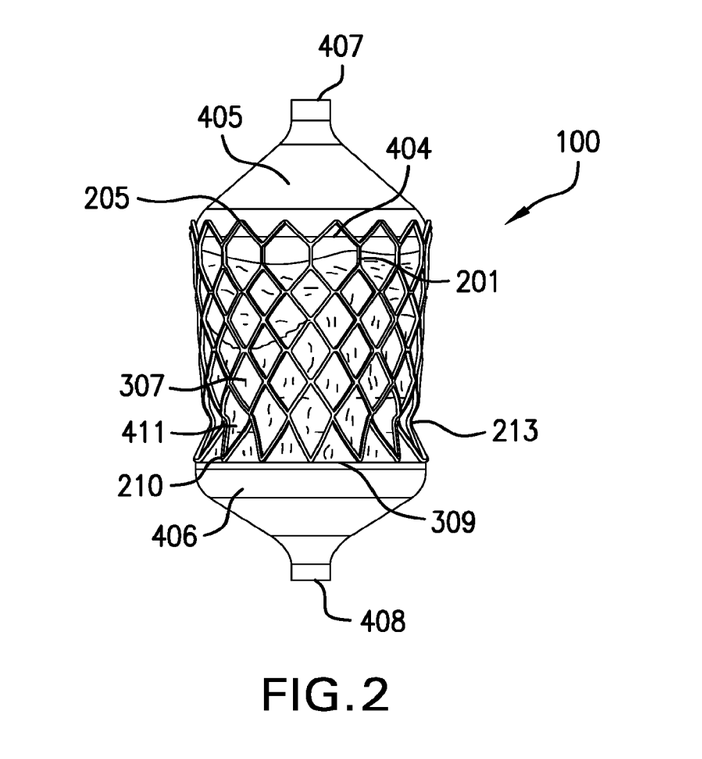
FIG. 2 is a side view of the assembly of FIG. 1.
Figure 3:
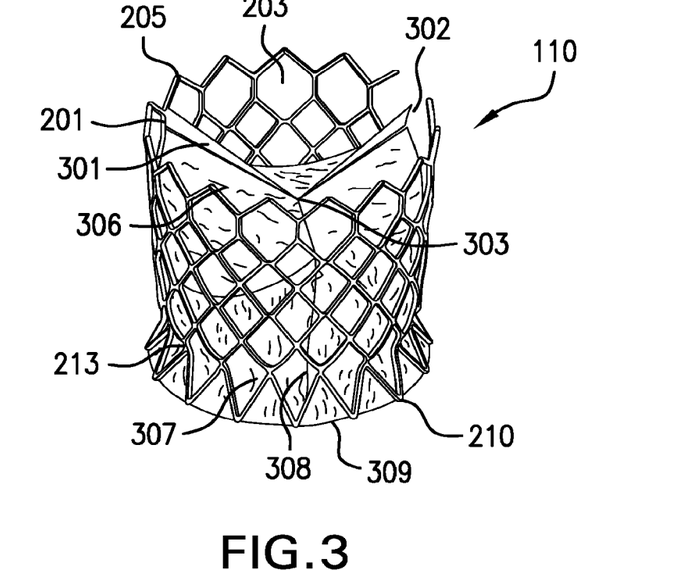
FIG. 3 is a perspective view of the heart valve assembly of FIG. 1.
Figure 4:
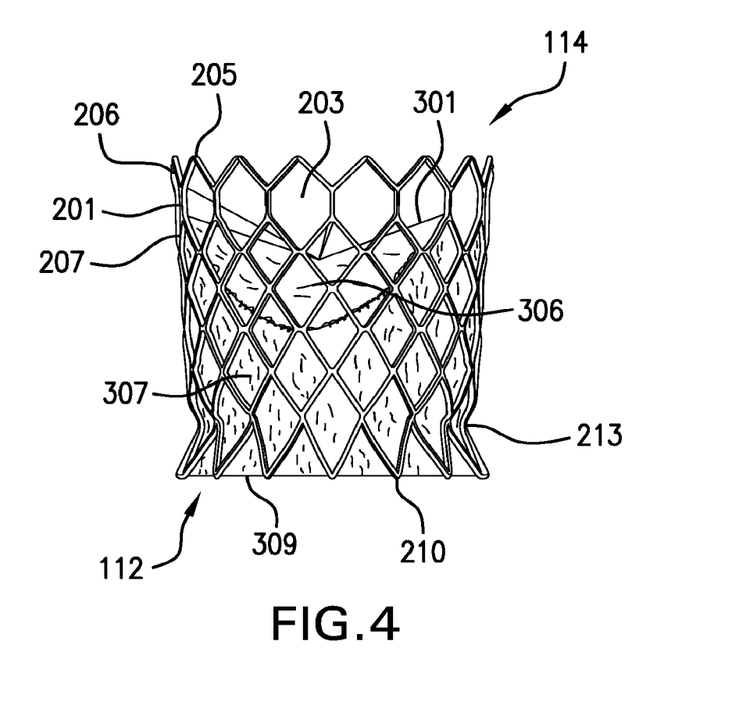
FIG. 4 is a side view of the heart valve assembly of FIG. 3.
Figure 5:
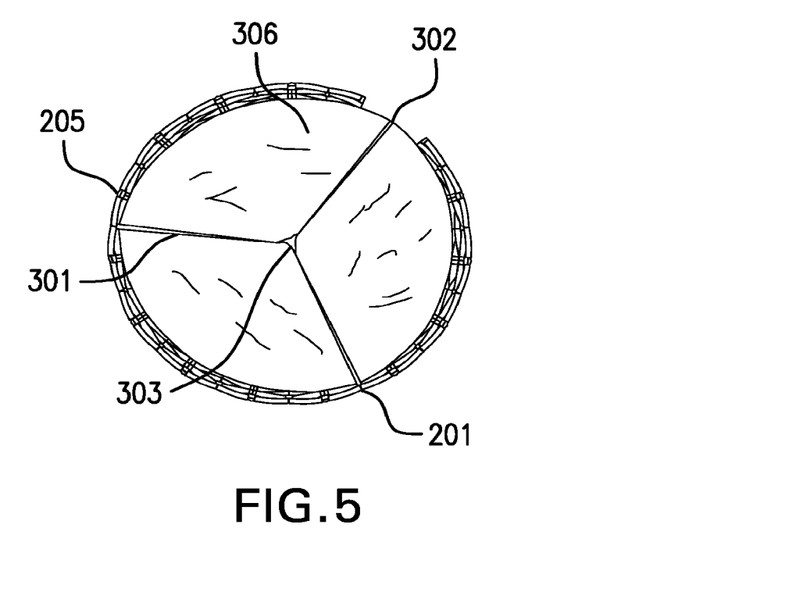
FIG. 5 is a top view of the heart valve assembly of FIG. 3.

FIGS. 1-2 illustrate a system 100 according to the present invention that includes a balloon-expandable prosthetic heart valve assembly 110 carried on an expandable member 400 for deployment at a valve annulus location inside a patient, which in the present invention can be the aortic annulus. FIGS. 3-5 illustrate an exemplary balloon-expandable prosthetic heart valve assembly 110 having an inflow or distal end 112 and an outflow or proximal end 114. The heart valve assembly 110 includes an outer stent-frame 200 (see also FIGS. 6-11) supporting a leaflet assembly 300 (see also FIGS. 12-15). FIGS. 3-4 show the heart valve assembly 110 in its expanded or operational shape, wherein the stent-frame 200 generally defines a tube and there are three leaflets 306 attached thereto and extending into the cylindrical space defined within to coapt against one another. In the heart valve assembly 110, three separate leaflets 306 are part of the leaflet assembly 300 and are each secured to the stent-frame 200 and to the other two leaflets along their lines of juxtaposition, or commissures. Of course, a whole bioprosthetic valve such as a porcine valve could also be used. In this sense, "leaflets" means separate leaflets or the leaflets within an entire xenograft valve.

Referring to FIGS. 1-11, the stent-frame 200 has an anchoring section 220 and an outflow section 230. The leaflet assembly 300 would be secured within the anchoring section 220. The anchoring section 220 has a distal annulus section 222 and a support section 224. The entire anchoring section 220 is defined by a generally annular body having a plurality of four-sided or diamond-shaped cells 202. Each cell 202 is formed by four struts 211 connected at connection points or nodes 212.

Figure 6:
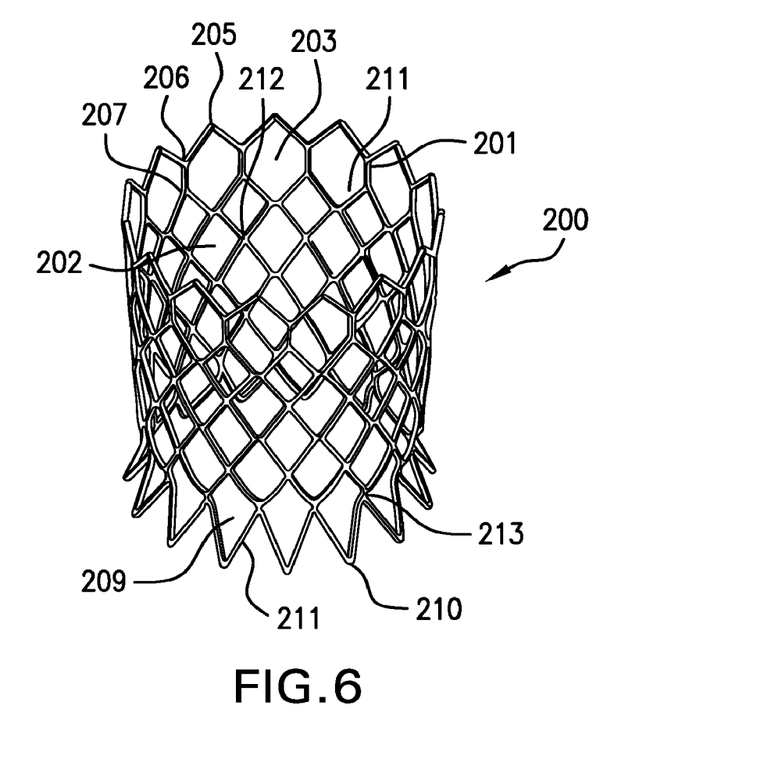
FIG. 6 is a perspective view of the stent frame of the heart valve assembly of FIG. 3.
Figure 7:
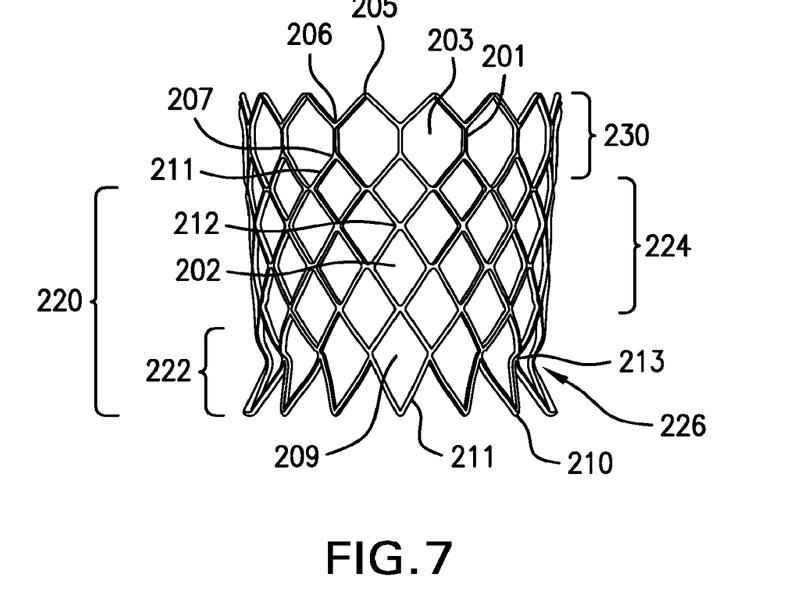
FIG. 7 is a side view of the stent frame of FIG. 6.
Figure 8:
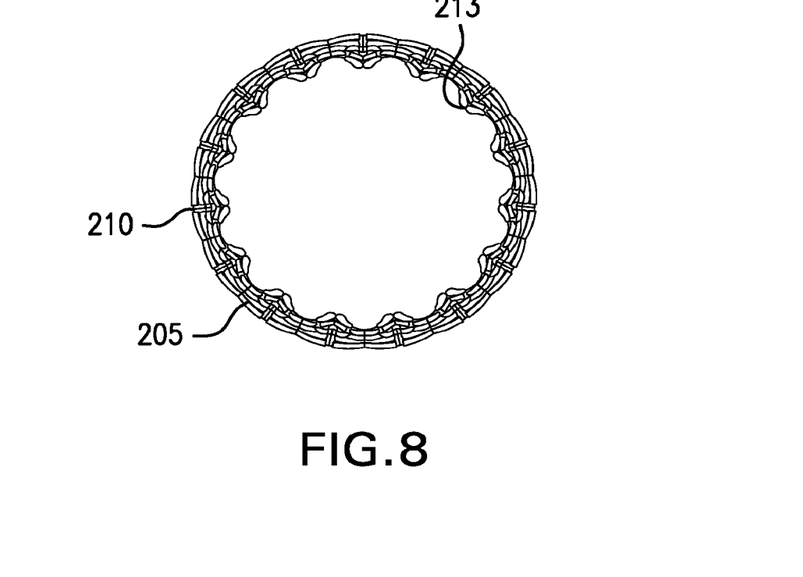
FIG. 8 is a top view of the stent frame of FIG. 6.
Figure 9:
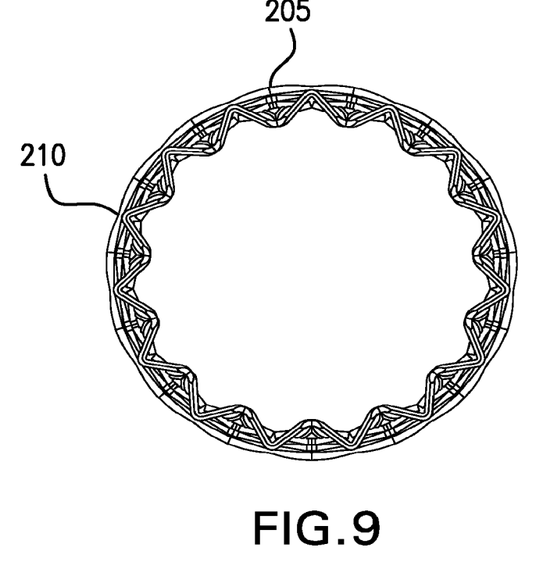
FIG. 9 is a bottom view of the stent frame of FIG. 6.

The annulus section 222 is primarily defined by the distal-most row of cells 209 that has a distal-most annular ring of alternating peaks 210 and valleys 213. The row of cells 209 has a concave inflection 226, with the row of peaks 210 having the greatest diameter and the row of valleys 213 having the smallest diameter and being the innermost valley of the concave inflection 226. Thus, the distal-most row of struts that alternate between the peaks 210 and the valleys 213 are curved or bent inwardly until they reach the valleys 213 (which act as inflection points), and then curve or bend outwardly towards the struts in the support section 224.

The support section 224 is defined by a plurality of rows (e.g., four rows as shown in FIG. 7) of cells 202 that can have generally the same diameter throughout (and slightly tapered, as described below) so as to be generally cylindrical. Each cell in the distal-most row of cells 202 shares a common strut with one adjacent cell of the row of cells 209. The sizes and shapes of the cells 202 can be generally the same or consistent throughout the support section 224, with the cells 209 being generally larger than the cells 202. As a result, the annulus section 222 is more flexible than the support section 224.

The proximal-most ring of cells 202 in the support section 224 transitions to the outflow section 230. Each cell in the proximal-most row of cells 202 in the support section 224 shares a common strut with one adjacent cell of the row of cells 203 in the outflow section 230. The outflow section 230 is defined by a single row of cells 203, with each cell 203 having a generally hexagonal shape defined by six struts. The outflow section 230 has a proximal-most annular ring of alternating peaks 205 and valleys 206 that are connected to each other by angled struts 204, and the valleys 206 are connected via straight struts 201 to the nodes 207 that connect the common struts that are shared by the cells in the proximal-most row of cells 202 in the support section 224.

The cells 203 are generally larger than the cells 202, and can also be larger than the cells 209.

Figure 10:
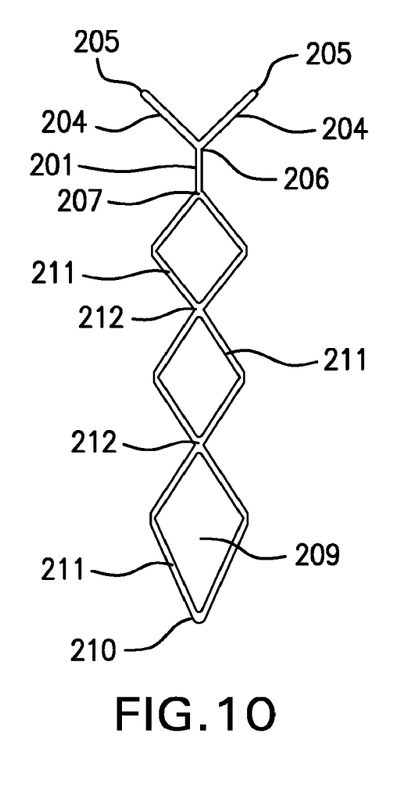
FIG. 10 is an isolated front view of showing one column of the cells of the stent-frame of FIG. 6.
Figure 11:
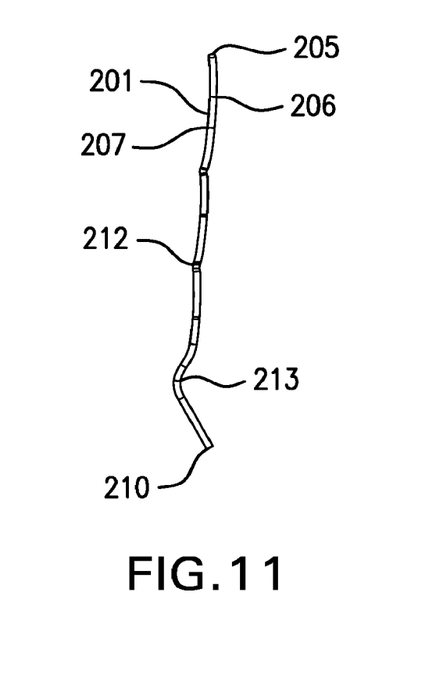
FIG. 11 is a side view of FIG. 10.
Figure 12:
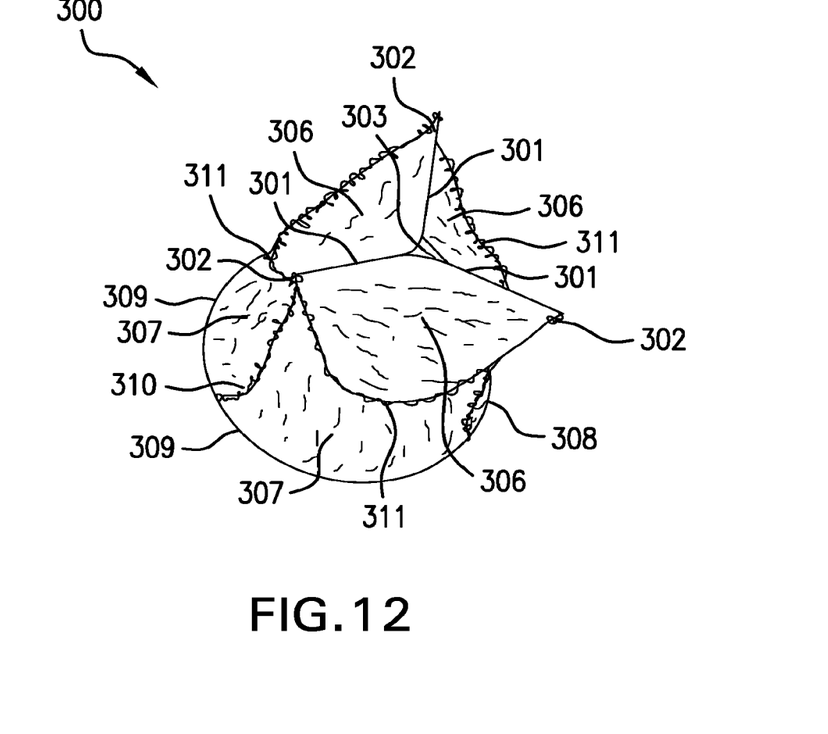
FIG. 12 is a perspective view of the leaflet assembly of the heart valve assembly of FIG. 3.
Figure 13:
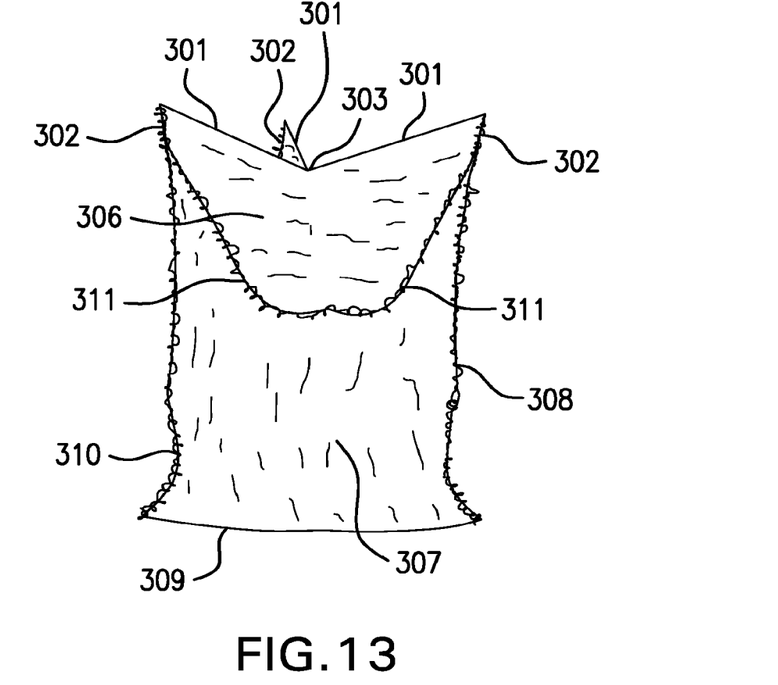
FIG. 13 is a side view of the leaflet assembly of FIG. 12.
Figure 14:
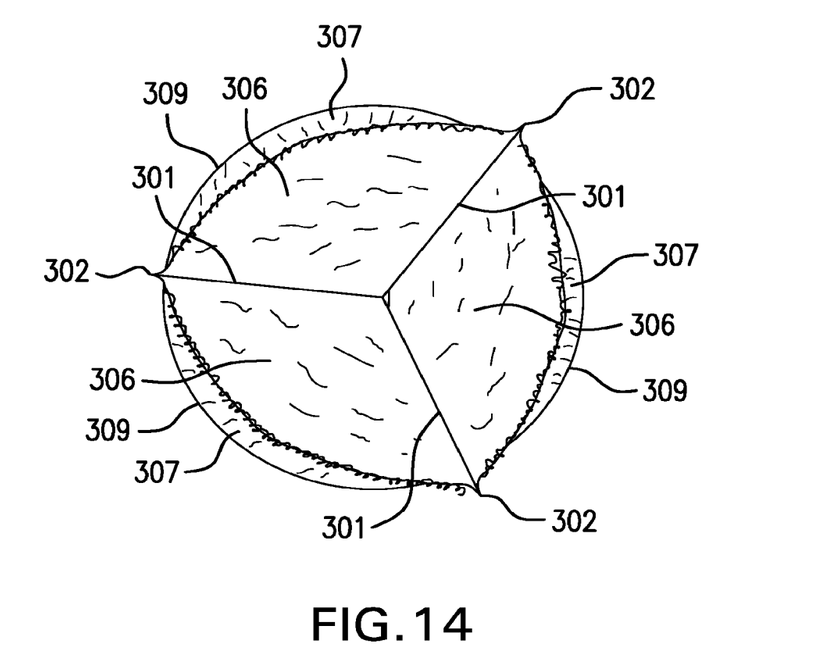
FIG. 14 is a top view of the leaflet assembly of FIG. 12.
Figure 15:
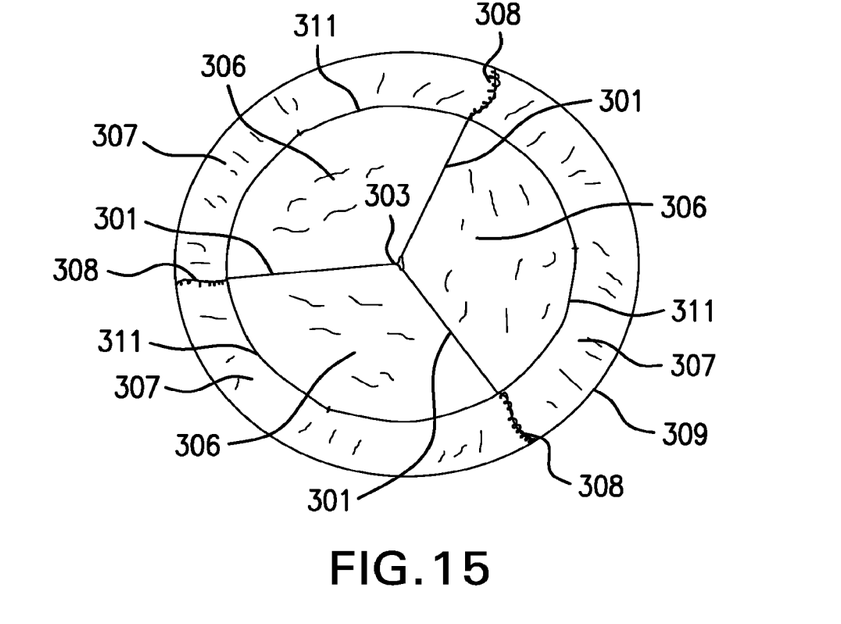
FIG. 15 is a bottom view of the leaflet assembly of FIG. 12.

FIGS. 10-11 are isolated views showing one column of the cells 209, 202 and 203 of the stent-frame 200. As best shown in FIG. 11, the struts that define the cells 209, 202 and 203 are not straight, but are instead slightly curved (i.e., have an arcuate shape), with the nodes 212 being inflected or extending slightly inwardly. In addition, as shown in FIG. 11, the overall diameter of the stent-frame 200 can gradually increase from the distal end of the support section 224 all the way to the proximal end of the outflow section 230 to form a very slight taper. The stent-frame 200 can have its largest diameter along the ring of peaks 210.

The shapes of the cells 203, 202 and 209 are provided for different purposes. For example, the hexagonal shape of the cells 203 is provided so that the cells 203 are more open for coronary access, and so that the outflow section 230 can be more flexible for the balloon 400 to expand. The cells 209 are configured to allow the annulus section 222 to be more flexible so that the inflow end 112 of the stent-frame 200 can be made more flexible so that it would be easier to create a neck when the balloon 400 expands.

Referring now to FIGS. 12-15, the leaflet assembly 300 is illustrated as having three leaflets 306, although it is also possible to provide a leaflet assembly that has two or four leaflets. An annular skirt having a plurality of skirt portions 307 supports the leaflets 306. In this embodiment, one skirt portion 307 is provided for each leaflet 306, with sutures 311 connecting the leaflet 306 to the skirt portion 307. Sutures 308 and 310 connect the adjacent edges of the skirt portion 307 to each other to form the annular skirt. An annular distal (inflow) edge 309 is defined by the skirt portions 307. Each leaflet 306 has two coaptation edges 301 that coapt with one coaption edge 301 from each of the other two leaflets 306, and each edge 301 has a skirt end 302 and an opposite coaptation end that meet near a central coaptation location 303.

The leaflets 306 and the skirt can be made from any known material that is commonly used for such leaflet assemblies, including porcine, bovine, or synthetic materials.

In the heart valve assembly 110, the flexible material forming the leaflets 306 attaches to the stent frame 200 via the skirt portions 307. Specifically, the skirt portions 307 are stitched or sutured to the anchoring section 220, and the skirt portions 307 extend throughout the distal annulus section 222 and the support section 224. As best shown in FIGS. 3-4, the leaflets 306 extend from a proximal-most position at the nodes 207, and curve distally towards the center of the support section 224. The skirt portions 307 extend from the peaks 210 proximally to different depths of the support section 224.

The bulk of the attachment structure between the stent-frame 200 and the leaflets 306 is located close to the inflow end 112. Each leaflet 306 preferably connects along an arcuate line between two points near the outflow end 114, and this arcuate line passes close to the inflow end 112, and thus the need for more sutures and the inflow end 112. As a result, the heart valve assembly 110 has a nonuniform expansion profile. More particularly, the inflow end 112 exerts substantially greater resistance to expansion on a balloon inflated from within than the outflow end 114. A cylindrical balloon inflated from within the heart valve assembly 110 will therefore expand faster or farther at the outflow end 114 than at the inflow end 112, because the outflow end 114 presents the path of least resistance.

As mentioned above, the present invention provides differently-shaped expansion members or balloons to ensure designed expansion of prosthetic heart valves. As mentioned above, balloons are almost universally used to deploy expandable heart valves. However, it is conceivable that a mechanical expansion member such as elongated fingers or hydraulically operated expanding members (i.e., not balloons) could be utilized. Therefore, the term "expansion members" is intended to encompass balloons and other variants.

In FIGS. 1-2 and 20-21, a balloon 400 mounts on a catheter and includes a proximal section 405, a central valve contact portion 420, and a distal section 406. The contact portion 420 includes an outflow portion 430, and neck portion 422, and a central portion 424. The proximal section 405 tapers with an increasing diameter distally from proximal end 407 to a first shoulder 440, which transitions into the outflow portion 430 at an annular transition line 404. The outflow portion 430 is adapted to receive the outflow section 230 of the stent-frame 200, and can have a generally constant diameter. The central portion 424 is adapted to receive the support section 224 of the stent-frame 200, and can be slightly tapered. The neck portion 422 is adapted to receive the annulus section 222 of the stent-frame 200, and is sized and shaped to match the size and shape of the intended annulus section 222. The neck portion 422 has an inflection zone 411 which is generally concave and which corresponds in size and shape to the concave inflection 226 on the stent-frame 200. The neck portion 422 the radially expands from the inflection zone 411 until it reaches a second shoulder 406 at an annular transition line 403. The second shoulder 406 transitions into the distal section 409, which gradually tapers in the distal direction towards a distal end 408. The balloon 400 can include a plurality of marker bands (not shown) therearound to facilitate registration of the heart valve assembly 110 with the balloon 400.

It is important to note that the terms "proximal and distal" in terms of the balloon is dependent on the direction of heart valve delivery into the annulus, because the heart valve leading end and thus balloon orientation on the catheter will be reversed in a heart valve replacement procedure that begins in a femoral artery as compared to a procedure that enters through the apex of the left ventricle.

The heart valve assembly 110 described above is positioned in its expanded state around the deflated balloon 400. Marker bands (not shown) are well-known in the art, and can be used to position the heart valve assembly 110 axially on the balloon 400 for proper inflation. Because of the non-uniform expansion profile of the balloon 400, the axial position of the heart valve assembly 110 is most important to ensure that the portions of the balloon 400 that are capable of applying the largest initial radially outward force are in registry with the stiffer areas of the heart valve assembly 110. In particular, the heart valve assembly 110 is positioned on the balloon 400 such that its inflow end 112 is positioned on the neck portion 422, and its outflow end 114 is positioned on the outflow portion 430. Subsequently, the heart valve assembly 110 is crimped around the balloon 400 so as to be ready for delivery into the body and advancement to the target implantation site. When the balloon 400 inflates, the neck portion 422 initially expands faster and ultimately farther than the outflow portion 430, thus compensating for the increased resistance to expansion of the heart valve assembly 110 and its inflow end 112. By careful calculation of the non-uniform resistance of the heart valve assembly 110 to expansion, the balloon 400 can be chosen so that the heart valve assembly 110 expands to its full diameter and proper operational shape (typically a cylinder or a shallow frusto-conical shape).

As will be appreciated by those of skill in the art, the specific shape of the expansion member/balloons described herein will differ depending on the valve construction.

Conventional balloons used to deploy prosthetic heart valves are made of clear nylon. Nylon balloons have a maximum expansion diameter which is important to avoid over-inflation and rupture. In addition, materials such as Pebax™ (polyether block amid) or PET (polyethylene terephthalate) can also be used.

The balloon 400 can be made according to any one of different approaches alone or in combination. For example, the balloon 400 can be pre-shaped using known techniques to the desired configuration and size in its expanded state. As another example, in U.S. Pat. No. 5,348,538, incorporated herein by reference, there is described a single layer balloon which follows a stepped compliance curve. The stepped compliance curves of the balloon provide a lower pressure segment where the balloon rapidly expands yielding inelastically, and a higher pressure region in which the balloon expands along a generally linear, low compliance curve.

Another approach to making the balloon 400 involves providing restriction members along the outer surface of the balloon which function to limit the expansion of the balloon at the location of these restriction members.

Yet another set of approaches involve varying the stiffness or thicknesses of the balloon material. For example, different materials with varying stiffness might be used to enhance the diameter at selected portions of the balloon 400. Materials such as PET, nylon, PEBAX™ or other polymers have adaptable or selectable ranges of stiffness. In some embodiments, the balloon 400 can have a wall material that is relatively stiff under at the inflow end 112, and relatively soft under the outflow end 114. Alternatively, the thickness of the wall of selected portions could be reduced to allow its expansion to the larger diameter. Another approach would be to expand the balloon 400 into a heated die with the desired end-shape. Yet another approach would be to apply coatings or additional layers, such as flexible, knitted sleeves, at strategic locations on the balloon's surfaces.

In addition, the balloon 400 can be doped with a radiopaque material. The doping is typically performed prior to balloon extrusion to ensure uniform distribution of the doping agent. Consequently, because the balloon itself is radiopaque, saline can be used to inflate it without addition of a viscous contrast media. Because of the lower viscosity of saline, the inflation/deflation time is greatly reduced.

In a typical operational sequence, the heart valve assembly 110 can be packaged in a separate sterile container from the balloon 400, or can be pre-crimped on the balloon 400 of a delivery catheter if dry tissue technology is used to treat the leaflets. In the operating room, the heart valve assembly 110 and balloon 400 are conjoined for implantation. This procedure requires careful positioning of the valve in its expanded state around the balloon, and crimping of the valve onto the balloon to a predetermined maximum diameter. The marker bands described above therefore greatly facilitate the step of positioning the valve over the balloon to ensure proper expansion.

Figure 16:
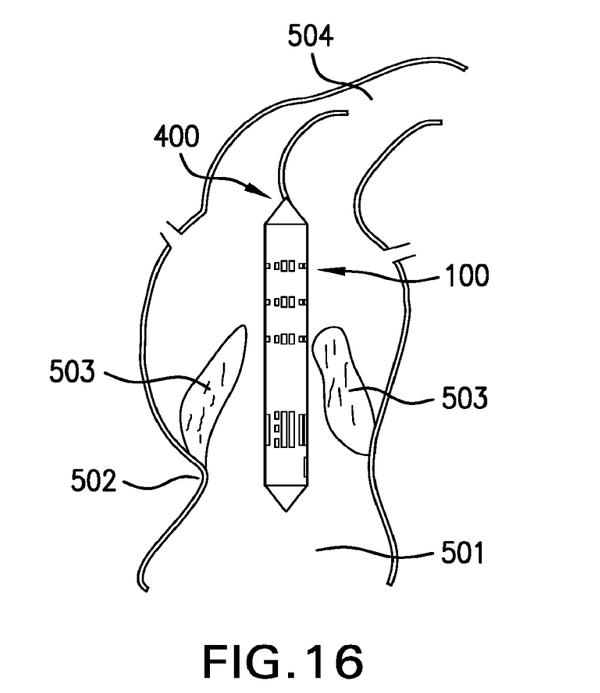
FIGS. 16-19 illustrate the steps for delivering and deploying the heart valve assembly of FIG. 3 at the aortic position of a human being.
Figure 17:
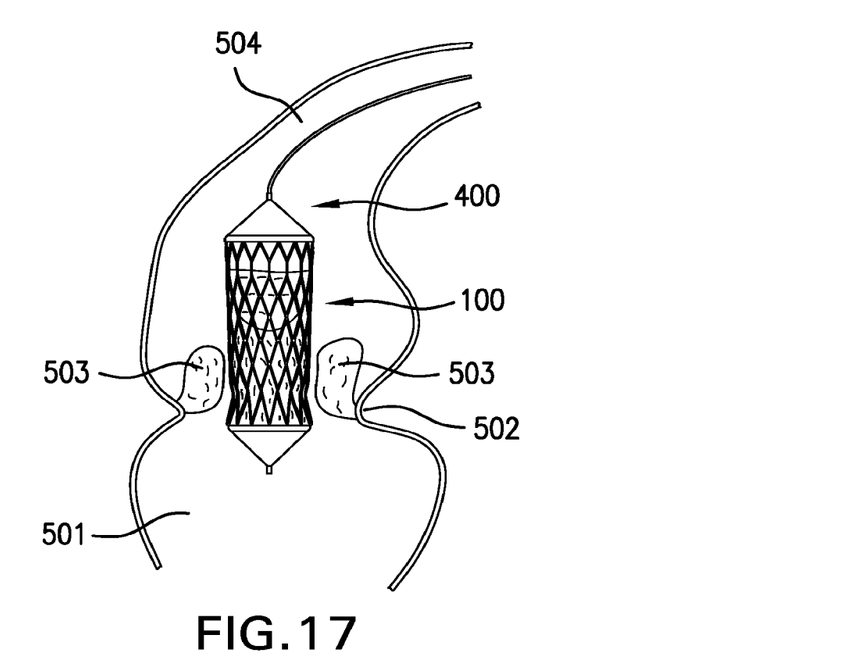
Figure 18:
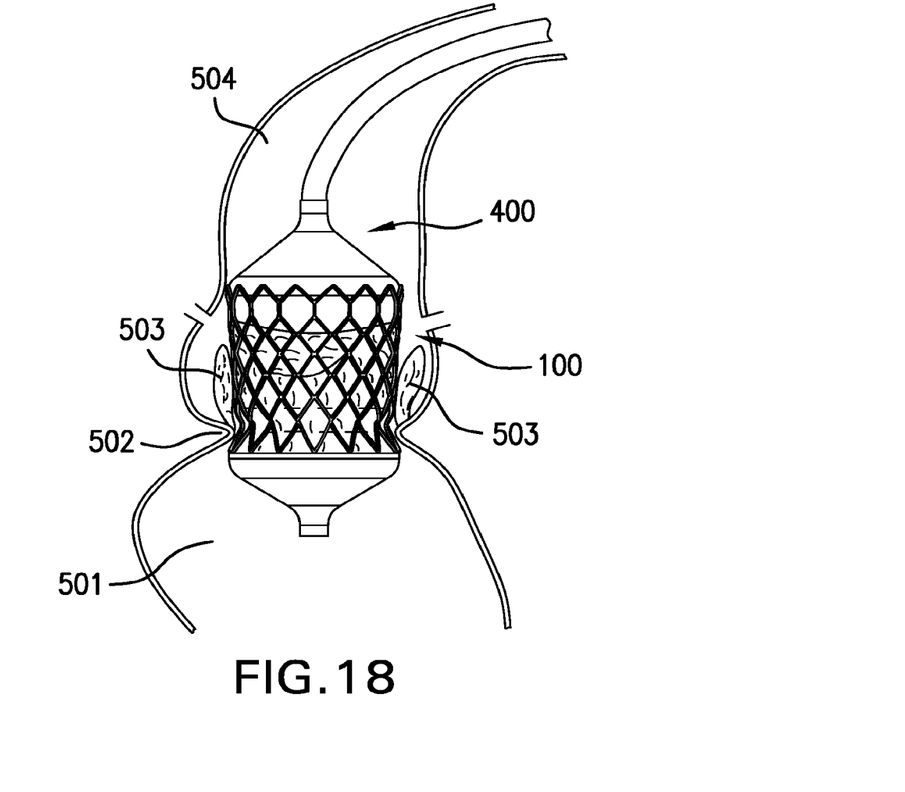
Figure 19:
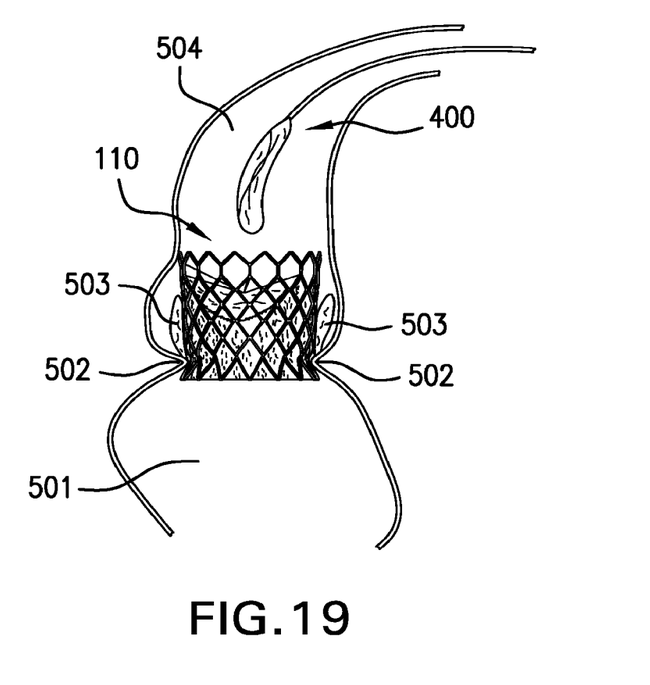
Figure 20:
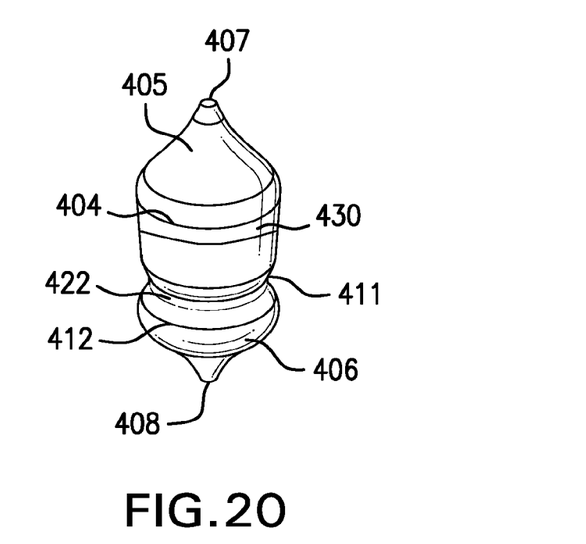
FIG. 20 is a perspective view of the expansion member of FIG. 1.
Figure 21:
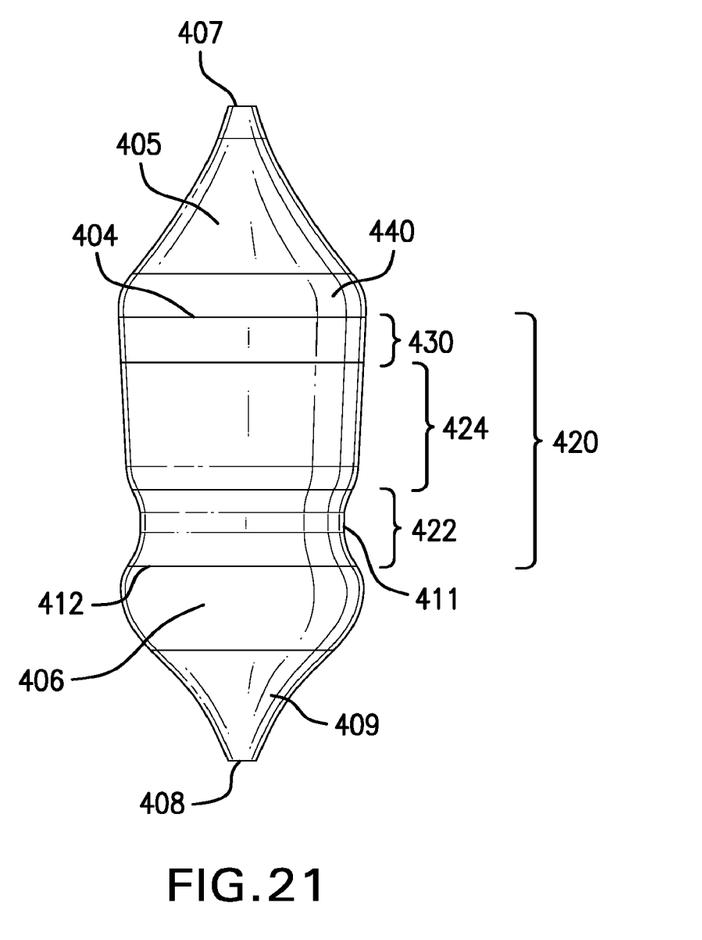
FIG. 21 is a side view of the expansion member of FIG. 20.

The combined heart valve assembly 110 and balloon 400 combination is then inserted into the body and advanced to the target implantation site. FIG. 16 shows access through the femoral artery and the ascending aorta 504. As shown in FIG. 16, the balloon 400 is carried on the distal end of a delivery catheter, and the heart valve assembly 110 and balloon 400 combination is delivered to the location of an aortic annulus 502 between the natural aortic leaflets 503. FIG. 17 shows the balloon 400 being expanded so that the heart valve assembly 110 also expands. FIG. 18 shows the heart valve assembly 110 fully expanded at the location of the annulus 502. At this position, the expanding distal end of the neck portion 422 (which carries the annulus section 222 of the stent-frame 200), as well as the distal section 406, of the balloon 400 extend into the left ventricle 501. The balloon 400 is then deflated and withdrawn (see FIG. 19). As shown in FIGS. 18 and 19, the annulus 502 is received inside the concave inflection 226 of the stent-frame 200, thereby securing the heart valve assembly 110 at the location of the aortic annulus 502.

As best shown in FIGS. 18-19, the heart valve assembly 110 is sized and shaped to be securely deployed at the aortic annulus 502 in a manner which reduces or minimizes PVL and maximizes the valve geographic EOA while reducing the stagnant blood near the cupid area during the diastolic cardiac phase when the valve leaflets 306 are closed. In addition, the balloon 400 is shaped to facilitate the delivery, expansion and implantation of the heart valve assembly 110.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for deploying a prosthetic heart valve at an aortic annulus of a patient's heart, system, comprising:
   providing a system comprising:
     a heart valve assembly, comprising:
       a stent-frame comprising an anchoring section and an outflow section, the anchoring section having a distal annulus section and a support section that is positioned between the distal annulus section and the outflow section,
       wherein the distal annulus section is defined by a single distal row of cells that has a distal-most annular ring of alternating peaks and valleys, with the distal row of cells having a concave inflection,
       wherein the outflow section is defined by a single proximal row of cells, with each cell in the proximal row of cells having a generally hexagonal shape, and having a proximal-most annular ring of alternating peaks and valleys, and
     a leaflet assembly stitched to the anchoring section; and
     a balloon on which the heart valve assembly is crimped, the balloon comprising:
       a proximal section and a distal section; and
       a central valve contact portion positioned between the proximal and distal sections, the contact portion having an outflow portion, a neck portion, and a central portion between the outflow portion and the neck portion, wherein the neck portion has an inflection zone that corresponds in size and shape with the concave inflection of the distal annulus section;

mounting the heart valve assembly on to the balloon in a manner where the outflow portion of the balloon receives the outflow section of the stent-frame, the central portion of the contact portion of the balloon receives the support section of the stent-frame, and the neck portion receives the annulus section of the stent-frame;

delivering the balloon and the mounted heart valve assembly to the aortic annulus; and expanding the balloon to cause the aortic annulus to be received inside the concave inflection.

* * * * *